United States Patent [19]

Rabinovitch

[11] Patent Number: 5,814,444
[45] Date of Patent: Sep. 29, 1998

[54] METHODS FOR MAKING AND USING SINGLE-CHROMOSOME AMPLFICATION LIBRARIES

[75] Inventor: Peter S. Rabinovitch, Seattle, Wash.

[73] Assignee: University of Washington, Seattle, Wash.

[21] Appl. No.: 486,647

[22] Filed: Jun. 7, 1995

[51] Int. Cl.⁶ .............................. C12Q 1/68; C12P 19/34; C07H 21/04

[52] U.S. Cl. .......................... 435/6; 435/91.2; 435/91.1; 536/24.3; 536/24.31; 536/24.33

[58] Field of Search ............................ 435/6, 91.1, 91.2; 536/22.1, 24.3

[56] References Cited

U.S. PATENT DOCUMENTS

| | | | |
|---|---|---|---|
| 5,427,932 | 6/1995 | Weier et al. | 435/91.2 |
| 5,461,907 | 10/1995 | Tench et al. | 73/105 |
| 5,491,224 | 2/1996 | Bittner et al. | 536/22.1 |

FOREIGN PATENT DOCUMENTS

| | | |
|---|---|---|
| 0 430 402 A2 | 6/1991 | European Pat. Off. |
| 0 545 459 A1 | 6/1993 | European Pat. Off. |
| WO 90/08821 | 8/1990 | WIPO |
| WO 93/06246 | 4/1993 | WIPO |

OTHER PUBLICATIONS

Marder et al, "Selective cloning of hybridoma cells for enhanced immunoglobulin production using flow cytometric cell sorting and automated laser nephelometry", Cytometry 11:498–505, 1990.

Djabali et al, "Laser microdissection of the fragilexregion: Identification of cosmid clones and of conserved sequences in this region", Genomics 10: 1053–1060, 1991.

VanDevanter et al., "Pure Chromosome–Specific PCR Libraries From Single Sorted Chromosomes," Proc. Natl. Acad. Sci. USA 91:5858–5862 (Jun. 1994).

Bohlander et al., "A Method for the Rapid Sequence–Independent Amplification of Microdissected Chromosomal Material," Genomics 13:1322–1324 (1992).

Boschman et al., "Identification of a Tumor Marker Chromosome by Flow Sorting, DNA Amplification In Vitro, and In Situ Hybridization of the Amplified Product," Genes, Chromosomes & Cancer 6:10–16 (1993).

Carter et al., "Reverse Chromosome Painting: a Method for the Rapid Analysis of Aberrant Chromosomes in Clinical Cytogenetics," J. Med. Genet. 29:299–307 (1992).

Cox et al., "Radiation Hybrid Mapping: A Somatic Cell Genetic Method for Constructing High–Resolution Maps of Mammalian Chromosomes," Science 250:245–250 (1990).

Cram, "Flow Cytogenetics and Chromosome Sorting," Human Cell 3:99–106 (1990).

Don et al., "'Touchdown' PCR to Circumvent Spurious Priming During Gene Amplification," Nucleic Acids Res. 19:4008 (1991).

Gray et al., "Flow Karyotyping and Chromosome Sorting," in Flow Cytometry and Sorting, eds. Melamed et al., Wiley-Liss, New York, pp. 503–529 (1990).

Jinno et al., "A Simple and Efficient Amplification Method of DNA with Unknown Sequences and its Application to Microdissection/Microcloning," J. Biochem. 112:75–80 (1992).

Kallioniemi et al., "Comparative Genomic Hybridization for Molecular Cytogenetic Analysis of Solid Tumors," Science 258:818–821 (1992).

Langford et al., "Chromosome Painting Using Chromosome–Specific Probes from Flow–Sorted Pig Chromosomes," Cytogenet. Cell Genet. 61:221–223 (1992).

Lebo et al., "High–Resolution Chromosome Sorting and DNA Spot–Blot Analysis Assign McArdle's Syndrome to Chromosome 11," Science 225:57–59 (1984).

Lengauer et al., "Chromosomal Bar Codes Produced by Multicolor Fluorescence In Situ Hybridization with Multiple YAC Clones and Whole Chromosome Painting Probes," Hum. Mol. Genet. 2:505–512 (1993).

Lisitsyn et al., "Cloning the Differences Between Two Complex Genomes," Science 259:946–951 (1993).

Meltzer et al., "Rapid Generation of Region Specific Probes by Chromosome Microdissection and Their Application," Nature Genetics 1:24–28 (1992).

Chang et al., "PCR Amplification of Chromosome–Specific DNA Isolated from Flow Cytometry–Sorted Chromosomes," Genomics 12:307–312 (1992).

Ostrander et al., "Construction of Small–Insert Genomic DNA Libraries Highly Enriched for Microsatellite Repeat Sequences," Proc. Natl. Acad. Sci. USA 89:3419–3423 (1992).

Pinkel et al., "Fluorescence In Situ Hybridization with Human Chromosome–Specific Libraries: Detection of Trisomy 21 and Translocations of Chromosome 4," Proc. Natl. Acad. Sci. USA 85:9138–9142 (1988).

Suijkerbuijk et al., "Fluorescent In Situ Identification of Human Marker Chromosomes Using Flow Sorting and Alu Element–Mediated PCR," Genomics 13:355–362 (1992).

Telenius et al., "Cytogenetic Analysis by Chromosome Painting Using DOP–PCR Amplified Flow–Sorted Chromosomes," Genes, Chromosomes & Cancer 4:257–263 (1992).

(List continued on next page.)

Primary Examiner—W. Gary Jones
Assistant Examiner—Jeffrey Fredman
Attorney, Agent, or Firm—Klarquist Sparkman Campbell Leigh & Whinston, LLP

[57] ABSTRACT

Methods for making chromosome-specific libraries from single chromosomes are disclosed in which a single flow-sorted chromosome (or subchromosomal fragment) is efficiently collected, and DNA extracted from the chromosome is amplified, e.g., by PCR. After they are produced, the resulting libraries are screened, e.g., by in situ hybridization or hybridization to a chromosome spot blot, to identify libraries that arise from the chromosome (or subchromosomal fragment) of interest. The single-chromosome amplification libraries and individual DNA sequences from the libraries are useful, for example, for cytogenetic analysis and cancer diagnostics.

15 Claims, No Drawings

OTHER PUBLICATIONS

VanDevanter et al., "Recombination Between Separate MYC Amplification Structures in COLO320 Cells," *Genes, Chromosomes & Cancer* 6:190–197 (1993).

Van Dilla et al., "The National Laboratory Gene Library Project," in Gray, ed., Flow Cytogenetics, Academic Press, New York, pp. 257–274 (1989).

Vooijis et al., "Libraries for Each Human Chromosome, Constructed from Sorter–Enriched Chromosomes by Using Linker–Adaptor PCR," *Am. J. Hum. Genet.* 52:586–597 (1993).

Wienberg et al., "Molecular Cytotaxonomy of Primates by Chromosomal In Situ Suppression Hybridization," *Genomics* 8:347–350 (1990).

Wienberg et al., "Homologies in Human and *Macaca fuscata* Chromosomes Revealed by In Situ Suppression Hybridization with Human Chromosome Specific DNA Libraries," *Chromosoma* 101:265–270 (1992).

METHODS FOR MAKING AND USING SINGLE-CHROMOSOME AMPLFICATION LIBRARIES

ACKNOWLEDGMENT OF GOVERNMENT SUPPORT

This invention was made with government support under grants no. AG 10917 and DK 32971, awarded by the National Institutes of Health. The government has certain rights in this invention.

TECHNICAL FIELD

This invention is related to the field of chromosome-specific libraries and cytogenetic analysis using chromosome-specific nucleic acid probes or primers.

BACKGROUND ART

Chromosome-specific DNA libraries have a growing number of applications in molecular genetics and cytogenetics. However, producing chromosome-specific libraries by presently available methods is difficult and labor intensive.

The standard approach to preparing chromosome-specific libraries employs flow cytometry to isolate relatively pure preparations of a chromosome of interest (Cram, Hum. Cell 3:99–106, 1990; Vooijs et al., Am. J. Hum. Genet. 52:586–597, 1993; Gray and Cram, in Flow Cytometry Sorting, eds. Melamed et al., Wiley-Liss, New York, 1990, pp. 503–530; Chang et al., Genomics 12:307–312, 1992; Langford et al., Cytogenet. Cell Genet. 61:221–223, 1992) from a preparation containing hundreds of thousands of individual chromosomes (Van Dilla et al., in Gray, ed., Flow Cytogenetics, Academic Press, New York, pp. 257–274, 1989). DNA amplification, e.g., by the polymerase chain reaction (PCR), is then used to manufacture libraries from the flow-sorted chromosomes (Chang et al., Genomics 12:307–312, 1992; Vooijs et al., Am. J. Hum. Genet. 52:586–597, 1993; Telenius et al., Genes, Chromosomes & Cancer 4:257, 1992; Boschman et al., Genes, Chromosomes and Cancer 6:10–16, 1993; Suijkerbuijk et al., Genomics 13:355–362, 1992). In order to make a truly "chromosome-specific" library, pure sorted chromosomes are required. In order to prepare a pure population of a single chromosome by flow cytometry, the DNA fluorescence of the desired chromosome must be distinct from that of all other chromosomes. In many species (e.g., rodents, dogs, and non-human primates) many chromosomes are so similar in size that it is impossible to separate them by flow sorting. Moreover, hundreds or thousands or chromosomes must be sorted, making it impossible to prepare chromosome-specific libraries from small tissue samples such as those available from individual solid tumors.

Another approach to the preparation of chromosome-specific libraries has relied on the existence of appropriate somatic cell hybrids (e.g., rat-human hybrid cell lines) that contain one or a few distinct human chromosomes (Cram, Hum. Cell 3:99–106, 1990; Vooijs et al., Am. J. Hum. Genet. 52:586–597, 1993). In most cases, however, useful inter-species cell lines do not exist.

There have also been attempts to produce libraries from subchromosomal regions or "bands." Such libraries have been made for some human chromosomes, most successfully by using Yeast Artificial Chromosomes (YACS) that have been identified as corresponding to a region of interest on a particular chromosome (Lengauer et al., Hum. Mol. Genet. 2:505–512, 1993).

It has also been proposed to make such subchromosome libraries by microdissection and chromosome scraping (Meltzer et al., Nat. Genet. 1:24–28, 1992; Bohlander et al., Genomics 13:1322–1324, 1992) followed by PCR amplification. However, these techniques are labor intensive and require exact identification of chromosome regions prior to the dissection of multiple chromosomes. In addition, DNA sequence representation in libraries from scraped chromosomes is much poorer than from sorted chromosomes, presumably due to the degraded or more inaccessible state of the fixed, scraped DNA (Jinno et al., J. Biochem. Jul. 112:75–80, 1992). Moreover, it is usually not possible to discriminate between alleles by these methods.

It is also been proposed to generate subchromosome DNA libraries using radiation hybrids (Cox et al., Science 250:245–250, 1990). However, this method, too, is labor intensive and requires extensive screening to find the desired fragment size.

For these and other reasons, improved methods to produce chromosome- and subchromosome-specific libraries are greatly needed.

SUMMARY OF THE INVENTION

Previously described methods for producing chromosome-specific libraries have started with chromosomal populations and have yielded libraries each containing a large number of individual chromosomes or subchromosomal fragments. The present invention provides methods and compositions related to the generation of libraries each containing a single chromosome or subchromosomal fragment. In order to produce the libraries, chromosomes are flow sorted and the sorted chromosomes are individually collected. Each chromosome can then be fragmented, e.g., by digestion with a restriction enzyme, and the fragments can be amplified, e.g., by the ligation-adaptor PCR technique, to make a library of amplified fragments. Each single-chromosome amplification library thus produced can then be screened to determine its chromosomal origin, e.g, by fluorescence in situ hybridization (FISH) or by hybridization to a chromosome dot blot.

Libraries can also be made from subchromosomal fragments, including chromosome bands, regions, etc. Chromosomes are fragmented, e.g., by mechanical shearing, and the subchromosomal fragments are flow sorted and separately collected. Each of the sorted subchromosomal fragments can then be further fragmented, e.g., by restriction-enzyme digestion, and amplified to produce a library of fragments from each sorted subchromosomal fragment. The libraries can then be screened to identify a library that is specific for the desired chromosome band, region, etc.

Because each library is derived from a single chromosome (or subchromosomal fragment), its purity is assured. Moreover, only small numbers of chromosomes are needed as starting materials, allowing libraries according to the present invention to be produced, for example, from solid tumors or primary tumor cultures.

It is also an object of the invention to provide libraries produced by these methods, as well as DNA molecules that comprise such libraries, and probes and primers comprising portions of such DNA molecules. These libraries, library members, and portions thereof find use in a number of applications, as described in greater detail below.

DETAILED DESCRIPTION OF THE INVENTION

Preparation of "Single-chromosome Amplification Libraries"

The present invention overcomes the problems inherent in previous methods of preparing chromosome-specific libraries by preparing libraries from single flow-sorted chromosomes. DNA extracted at high efficiency from each of the single chromosomes is separately amplified by PCR (or other amplification method) and the amplification products are screened to identify an amplification product representing the chromosome of interest.

The starting material for library preparation is a population of chromosomes from a biological sample. Flow sorting (or cytometry) serves: (1) to efficiently separate and deliver the chromosomes to a desired physical location, such as individual tubes, wells of a 96-well microtiter plate, etc.; and (2) to enrich the chromosome population for the chromosome of interest. Enrichment is accomplished by sorting the chromosomes by size, based on the relative fluorescence intensity of DNA molecules of different sizes. The specificity of the single-chromosome amplification library for a single chromosome is assured even when the resolution of different chromosomes is poor, because only one chromosome is sorted per library. In fact, enrichment of the chromosome population is unnecessary if an efficient means for library screening is available.

Libraries can be similarly prepared from fragments of a chromosome, i.e., subchromosomal fragments (chromosome regions, bands, etc.). To prepare such libraries, one or more chromosomes is fragmented by well-known means, e.g., mechanical shearing, treatment with agents known to cause DNA strand breakage and fragmentation such as gamma irradiation and bleomycin, or digestion with restriction enzymes having infrequent (e.g., 8-base) recognition sites.

Although one can perform PCR on chromosomal DNA or large subchromosomal DNA fragments, e.g., using random primers, it is preferable to produce smaller DNA fragments, ligate these smaller fragments to an adaptor sequence, then amplify the smaller fragments using PCR primers that hybridize specifically to the adaptor sequence to produce the library. In a preferred embodiment of the present invention, the ligation-adaptor PCR technique (Chang et al., Genomics 12:307–312, 1992; Lisitsyn et al., Science 259:946–951, 1993; Jinno et al., J. Biochem. 112:75–80, 1992) is employed. Both sorting and amplification can be conveniently performed in a single tube. In fact, where these steps are being carried out, for example, in the wells of a 96-well microtiter plate, it is possible to amplify the entire plate at the same time using an appropriate thermal cycler.

After the libraries are produced, they are screened to identify a library specific for a chromosome or subchromosomal fragment of interest ("target chromosome" or "target subchromosome fragment"). Such screening can be accomplished by any well-known method, e.g., by in situ hybridization (e.g., FISH) or hybridization or amplification using probes or primers specific for the target chromosome or subchromosome fragment.

Large numbers of libraries can be quickly and easily screened using chromosome "spot blots" as described in greater detail below.

Delivery of flow-sorted chromosomes to separate tubes is performed using an unmodified cell sorter and conventional procedures. The sorter is instructed using the usual computer interface to sort one object at a time, and the desired tube is placed in the usual sorting position for collecting the object. Collection of individual chromosomes (or subchromosome fragments) in separate tubes or wells can be accomplished manually or can be automated. For example, automated 96-well plate collectors are available as accessories to commercial instruments for speeding collection. These accessories are motorized x-y translators for positioning the plate under the sorter.

Preferably, where libraries are produced in multi-well plates, the entire plate is screened at once. Preferably, screening involves addition of one or more probes specific for the chromosome of interest to each of the wells. Greater sensitivity is obtained from using a complex mixture of multiple chromosome-specific probes. Such a mixture of probes is assembled from DNA sequences mapped to the chromosome (or subchromosomal fragment) of interest.

FISH can be more efficiently employed for screening for a library specific for a chromosome (or subchromosome fragment) by, for example, using multi-chambered slides (such as Lab-Tek 8-chambered slides, Nunc, Inc., Napersville, Ill.), each chamber holding one or more normal lymphocyte metaphase spreads (only one or a few of which would need to be examined), and hybridizing a different PCR product in each chamber. Alternatively, each PCR product can be pre-screened by hybridization to a chromosome dot-blot array.

The present invention provides a qualitative break with previous methods for producing chromosome-specific libraries. The specificity of a single-chromosome amplification library for a single chromosome is assured, because each library is generated from a single sorted chromosome or fragment and not from a population of chromosomes. In fact, no special expertise in chromosome sorting is required, since good results can be obtained even when different chromosomes or subchromosome fragments cannot be separately resolved by flow sorting.

Moreover, extremely small numbers of chromosomes are needed, allowing this technique to be used to generate single-chromosome amplification libraries from a small number of metaphase cells, as in characterizing chromosomal aberrations in primary tumor cultures.

In addition, one can readily produce and characterize chromosome band- or region-specific libraries and individual chromosome-specific DNA probes that hybridize at a variety of locations along a chromosome of interest.

Uses of the Methods and Compositions of the Invention

As mentioned above, single-chromosome amplification libraries (and individual DNA sequences derived from such libraries) have a growing number of applications in molecular genetics and cytogenetics, including serving as libraries of known chromosomal origin for screening genomic DNA or cDNA; as a source of useful probes for FISH and other techniques for cytogenetic analysis directed to evaluating chromosome aberrations; and for developing allele-specific libraries from individuals in order to better map and study genetic disease. In addition, the ability to rapidly produce such libraries, including allele-specific libraries, from individuals is extremely useful for mapping and studying genetic disease. These and other applications of the methods and compositions of the present invention are discussed in greater detail below.

Rapid allelotyping and allelic sequencing. The ability to analyze microsatellite repeat polymorphisms on libraries from a single chromosome is useful for rapid allelotyping and allelic sequencing, e.g., to identify affected regions or genes in individuals with genetic diseases, and can be combined for this purpose with strategies for subtraction of libraries (Lisitsyn et al., Science 259:946–951, 1993) generated from each somatic chromosome in affected individuals.

Identifying and characterizing chromosomal abnormalities. Fluorescence in situ hybridization (FISH) is a powerful cytogenetic tool for staining specific chromosomes in a manner that allows numerical and structural aberrations to be easily evaluated in either metaphase or interphase cells (Pinkel et al., Proc. Natl. Acad. Sci. USA 85:9138–9142, 1988). The characterization of cytogenetic aberrations in tumors has contributed to the understanding of carcinogenesis, tumor progression, and to clinical management decisions. The ability to produce a wider range of chromosome-specific, particularly band-specific, DNA probes according to the present invention is extremely useful for tumor cytogenetics.

A number of neoplasias and other conditions are characterized by genetic changes including chromosomal aberrations. The present invention makes it possible to quickly and easily generate chromosome band-specific FISH probes. Region sizes can be accurately chosen by using the flow cytometer to select the DNA fluorescence intensity of sorted fragments, and chromosomal locations can be determined, for example, by FISH.

There has been detailed cytogenetic analysis of hematologic malignancies (e.g., lymphomas and leukemias; Solomon et al., Science 254:1153–1160, 1991). By contrast, solid tumors have been difficult to evaluate for several reasons: the difficulty of establishing tumor cell cultures; poor growth of cultures; admixtures of cell types; and production by tumor cells of a matrix that prevents the spreading of chromosomes needed for cytogenetic analysis. The morphology of the chromosomes is often poor, the karyotype of solid tumors is usually complex, and the identification of the different components of structurally rearranged chromosomes is frequently impossible.

A "tumor marker chromosome" is a chromosome differing from a normal chromosome, for example, in size and/or banding pattern, that is characteristic of the cells in a particular tumor and is not found in normal cells. Such marker chromosomes frequently result from rearrangements and recombinations of portions of a normal chromosome or several normal chromosomes. Characterization of tumor marker chromosomes by serial painting with presently available libraries from normal human chromosomes requires good tumor chromosome morphology, is labor intensive, and does not identify which regions of individual chromosomes are represented in markers or the location of chromosomal aberrations such as breakpoints. Similarly, marker-chromosome microdissection requires numerous dissection procedures to assure good representation within a library. Comparative genomic hybridization (CGH), which can indicate relative amplification or deletion of DNA in the genome, has been proposed as an alternative means for analyzing marker chromosomes in solid tumors (Kallioniemi et al., Science 258:818–821, 1992). However, this technique also suffers from several drawbacks: (1) the composition and structure of individual chromosomes in a tumor is not identifiable; (2) rearrangements are not identifiable; and (3) the resolution of the location of breakpoints and the ability to detect small regions of DNA deletion or amplification is limited by the low signal-to-noise ratio.

There are several diseases that are associated with an increased risk of cancer by a multistep progression involving accumulated genetic changes, including ulcerative colitis (UC) (Rabinovitch et al., Lab. Invest. 60:65–71, 1989; Burmer et al., Cancer Commun. 3:167–172, 1991; Burmer et al., Env. Health Perspectives 93:27–31, 1991; Levine et al., Gastroenterology 101:1198–1210, 1991; Burmer et al., Gastroenterology 103:1602–1610, 1992, Reid et al., Gastroenterology 102:1212–1219, 1992; Rubin et al., Gastroenterology 103:1611–1620, 1992) and Barret's esophagus (Raskind et al., Cancer Res. 52:2946–2950, 1992). Standard cytogenetics in gastrointestinal malignancies has met with limited success (Raskind et al., Cancer Res. 52:2946–2950, 1992), primarily due to the difficulty in obtaining sufficient numbers of high-quality chromosome spreads. Knowledge of the cytogenetic abnormalities occurring at each histologic stage in progression to cancer (indefinite→low grade dysplasia→high grade dysplasia→cancer) can be used to direct efforts to characterize the molecular alterations associated with this progression.

Particularly useful for these purposes are molecular markers associated with early events in the neoplastic progression for defining the subset of patients that are at highest risk for development of cancer, so that clinical resources can be most efficiently focused on these highest risk patients. With UC, for example, patients with long-duration disease (>6 years) are known to be at increased risk for cancer, but following all of these patients with periodic intensive colonoscopic biopsy to find dysplasia or cancer in early curable stages is expensive and impractical. One early marker in UC is loss of heterozygosity of a region of the distal short arm of chromosome 8 (Chang et al., Am. J. Pathol. 144:1–6, 1994), the site of a putative tumor suppressor gene that may also be implicated in prostate and breast cancer. The location of this putative suppressor has been mapped by analysis of loss of heterozygosity of microsatellite repeat polymorphisms on chromosome 8p (Chang et al., Am. J. Pathol. 144:1–6, 1994). Additional polymorphic markers within this small region made available through the methods and compositions of the present invention are of considerable practical use in better defining the location of the putative suppressor gene in this region.

DNA probes that characterize specific chromosome aberrations in abnormal cells are readily produced using the methods and compositions of the present invention. The molecular characterization and cloning of chromosomal abnormalities, e.g., fusion genes and rearrangements present on marker chromosomes can be accomplished, for example, by using representational difference analysis (RDA, Lisitsyn et al., Science 259:946–951, 1993) to "subtract" normal chromosome libraries from the marker library.

In the case of UC, for example, disease progression is accompanied by the loss of chromosome 8p sequences. Microsatellite sequences detected in a library produced from fragments of chromosome 8 permit the identification of aberrant chromosome 8 marker chromosomes that have lost sequences from the 8p region. The use of single-chromosome sorting to generate marker-specific DNA libraries from marker chromosomes in UC thus complements conventional molecular genetic characterization of UC neoplasia.

The present invention facilitates the analysis of cytogenetic marker chromosomes of both hematologic malignancies and solid tumors. Unlike previously available methods, the present invention does not rely on the availability of large numbers of mitotic cells and good chromosome morphology for cytogenetic analysis. One directly identifies the composition of complex tumor marker chromosomes in a single experiment, rapidly identifying and characterizing chromosomal abnormalities such as breakpoint regions, fusions, and rearrangements. FISH analyses of marker-specific DNA libraries can be performed on normal metaphase cells, including "reverse" chromosome painting (Telenius et al., Genes, Chromosomes & Cancer 4:257, 1992; Carter et al., J. Med. Genet. 29:299–307, 1992), in which DNA libraries specific for tumor chromosomes are constructed as described herein and used for FISH to normal chromosomes. The present invention is therefore useful for cancer diagnosis, to follow tumor progression, and to manage the treatment of the disease in an individual patient.

There are a number of considerations for applying the present invention for rapid FISH karyotyping of human tumors or primary tumor cultures, in which only small numbers of metaphase chromosomes are available. Only a subset of primary tumors develop into permanent cell lines, and many of these may be overgrown by fibroblasts. In addition, the karyotype may diverge in long-term culture. Abnormal mucosa from UC can be used as a model system for application of single-chromosome sorting and DNA library production from primary tissue. For primary culturing, the tumor is minced, digested with collagenase, and placed in culture with colcemide for four hours. Metaphase chromosomes are sorted from these primary cultures.

Chromosomes can be distinguished from cellular and nuclear debris on the basis of the different light-scattering and pulse-shape properties of chromosome and debris. Whereas chromosomes are small and compact, most debris-related signals are due to autofluorescence of larger cellular fragments or small DNA fragments adhered to such cellular debris. The forward and right-angle scatter of this debris is larger than the very low scatter of chromosomes, and the pulse-width (or peak/area ratio) of the fluorescence signals from the debris is larger than that of chromosomes. Both scatter and pulse-width are used to separate debris from chromosome signals by gating.

Also of assistance in distinguishing chromosomes from cellular and nuclear debris is the use of anti-centromere antibodies (Schmitz et al., Cytometry 13:478–484, 1992) which stain only chromosomes and not debris, even DNA debris. DNA is stained with DAPI or Hoechst dye and FITC-antibody for simultaneous analysis.

In addition, to further aid in distinguishing chromosomes from debris, other cell constituents that form debris can be simultaneously labeled with a red fluorochrome, if necessary. Protein can be labeled with sulfo-rhodamine 121 and membranes with DPH-phosphatidylcholine (Molecular Probes), for example.

Finally, metaphase chromosomes can be distinguished from fragments of interphase DNA by DNA conformation-sensitive staining (e.g., by using Acridine Orange, Darzynkiewicz et al., Exp. Cell. Res. 110:201, 1977).

Chromosomal "bar codes". Simultaneous use of a number of such chromosome band-specific probes allows unique chromosomal "bar codes" to be produced to confirm chromosomal aberrations and breakpoints, even in interphase cells (Lengauer et al., Hum. Mol. Genet. 2:505–512, 1993).

Comparative cytogenetics and molecular taxonomy and phylogeny. Human chromosome probes have in the past been useful in FISH studies of primate cytotaxonomy (Wienberg et al., Genomics 8:347–350, 1990; Wienberg et al., Chromosoma 101:265–270, 1992). The ability to use single-chromosome sorting to rapidly generate chromosome-specific probes to diverse species provides important reagents for research in comparative cytogenetics and molecular phylogeny.

One application of the methods and compositions of the present invention is to identify and clone microsatellite repeat polymorphisms within single-chromosome amplification libraries. These polymorphisms are useful for developing linkage maps in non-human species and for increasing the density of current linkage maps in human and non-human species.

It is possible to screen for the presence of known markers, although only a subset of the much smaller number of such loci which have been characterized in non-human systems are represented in libraries generated by Sau 3A digestion and ligation-adaptor PCR of single sorted chromosomes.

For this reason, a technique for the selective enrichment and cloning of chromosome-specific polymorphic short tandem repeat sequences from non-human chromosome libraries (Ostrander et al., Proc. Natl. Acad. Sci. USA 89:3419–3423, 1992) is preferably employed. The combination of the method of library construction from single chromosomes together with the method for making libraries enriched for polymorphic markers make it possible to generate high-density maps for new species in a rapid fashion.

Many non-human model systems for the study of human genetic diseases have been described, with large colonies of afflicted non-human individuals available for the mapping and cloning of genetic loci that correspond to these diseases. The ability to analyze microsatellite repeat polymorphisms in libraries generated from a single chromosome is useful for more rapid allelotyping and allelic sequencing. Moreover, genomic subtraction strategies as applied to subtraction of libraries (Lisitsyn et al., Science 259:946–951, 1993) generated from individual chromosomes from non-human models for human diseases allows one to identify, analyze, and clone genes associated with the diseases. This, in turn, allows one to identify, analyze, and clone the corresponding human genes.

Previously described human microsatellite (short tandem repeat) polymorphisms (STRP) cannot be used to construct linkage maps in non-human species. Single-chromosome amplification libraries, however, are useful for creating high-density genetic maps for a large variety of non-human species.

Simple sequence repeats are polymorphic in repeat number within populations yet sufficiently stable within pedigrees to be useful as genetic markers (Litt and Luty, Am. J. Hum. Genet. 44:397–401, 1989; Weber and May, Am. J. Hum. Genet. 44:388–396, 1989).

One particularly useful type of STRPs is the $(CA)_n$ repeats, which are found with a frequency of about $\frac{1}{30}$ Kb in mammalian genomes (Stallings et al., Genomics 10:807–815, 1991; Beckman and Weber, Genomics 12:627–631, 1992). $(CA)_n$ repeats are typically measured by PCR-based assays that detect the length polymorphisms that characterize different alleles. They are extremely polymorphic and often have 10–12 alleles in the population (Weber and May, Am. J. Hum. Genet. 44:388–396, 1989; Luty et al., Am. J. Hum. Genet. 46:776–783, 1990). In the canine genome, for example, approximately 150 $(CA)_n$ repeats have been generated to date. Since they were generated using libraries prepared from total chromosomal DNA, their chromosomal location is unknown. Unfortunately the canine genome is made up of a large number of small acrocentric chromosomes, rendering conventional FISH-based strategies for placing the markers useless. The approach described above and in the Examples below facilitates the rapid generation of large numbers of such markers that are useful for mapping genetic traits.

Chromosome spot blots. Chromosome "spot blots" are created by attaching chromosomes or individual sequences specific for a chromosome or chromosomes to a solid support, e.g., a hybridization filter membrane at identifiable positions in an array. Chromosome "spot blots" have been previously created by directly sorting various chromosome types by using standard flow cytometry to sort chromosomes from a large chromosome population and spotting the sorted chromosomes onto a hybridization filter membrane (Lebo et al., Science 225:57–59, 1984).

In an improvement of this chromosome "spot blot" technology, single-chromosome amplification libraries (or members of such libraries), preferably libraries that have been depleted of repetitive DNA, are attached to a hybridization filter membrane.

For maximum hybridization sensitivity, it is preferable to use chromosomal DNA that has been restricted and amplified, e.g., by PCR, using the same enzymes as have been used for amplification of the uncharacterized chromosomal DNA. Such DNA shares maximum homology with DNA derived from the same chromosome and thus results in the greatest positive hybridization signal, even when only small fragments of a chromosome are sorted or even if only a fragment of a chromosome is represented, e.g., in a tumor-marker chromosome.

Preferably, the single-chromosome amplification libraries or probes used to create a chromosome spot blot have been depleted of repetitive DNA.

It is possible to quickly screen large numbers of libraries by labeling each library, hybridizing it to a chromosome spot blot, and identifying the position on the blot to which the library hybridizes. For example, such a blot can contain a library representing each of the human chromosomes, preferably depleted of repetitive sequences, in a different position. The pattern of hybridization of each library produced from human tissue establishes the chromosomal origin of the library.

In a preferred embodiment, PCR-amplified chromosomal DNA is dot-blotted onto a hybridization membrane in a small, dense array. The size of such an array is small enough to be rolled up and placed into one well of a 96 well plate. Each of 96 such arrays is washed after hybridization, and all 96 developed at once. To develop by autoradiography, the last few cycles of PCR used in library amplification incorporate a $^{32}$P-labeled dNTP; to develop by enzyme-coupled avidin, the last cycles of PCR used in library amplification would incorporate biotin dUTP.

Ideally, amplified DNA from a single sorted normal chromosome produces only a single positive hybridization signal ("dot") on such an array. DNA amplified from a marker chromosome that is the product of chromosome translocation produces more than one positive dot, each dot indicating the chromosomal origin of the DNA making up the abnormal chromosome.

A chromosome dot blot can also be employed in a "reverse" strategy for library screening: single-chromosome amplification libraries are dotted onto a nylon membrane and probed with a chromosome of interest (i.e., with a probe specific for the chromosome, preferably depleted of repeated sequences). Such an approach is discussed in Example 7, below.

The speed and efficiency of screening single-chromosome amplification libraries by using chromosomal "dot blots" can be improved by using alternative blot geometries. For example, spot blots are made on 2 mm x 30 mm membrane strips, one of which is curled into each of the 96 individual PCR wells of a 96-well microtiter dish. After hybridization, all 96 blot strips are recovered, unrolled, and autoradiographed at once. Subsequently, only wells containing PCR products that hybridize to a chromosome-specific probe are analyzed by FISH.

Such membrane strips can be made by cutting many strips from a single larger membrane sheet that has had different single-chromosome amplification libraries applied in "stripes" (such as the red stripes on the US flag) that are applied using wells in a custom template. The sheet is rolled and many thin strips are then cut from this rolled sheet. A strip is placed in each one of 96 microtiter wells, each of which has previously been used for amplification of a single chromosome. The last 5 cycles of PCR in these wells include either $^{32}$p dNTP or biotin-dUTP. The strips are hybridized to the well contents for 24 hours. Using a multiwell pipetter, the well contents are transferred to a new plate for storage and the membrane strips in the original wells are washed. For autoradiography, the strips are removed, spread onto a gel dryer, and then autoradiographed.

It is preferred to use biotin-dUTP labeled PCR products in the wells. If so, after the strips are washed, they are incubated with avidin-peroxidase or avidin-alkaline phosphatase, and then developed (still in the well) by addition of either hydrogen peroxide and 4-chloro-1-naphthol or 5-bromo-4-chloro-3-indolyl phosphate, respectively. As each strip is removed from the well, the strip is visually "read" by observation of the position of one or more dark spots.

DEFINITIONS AND METHODS

The following definitions and methods are provided to better define the present invention and to guide those of ordinary skill in the art in the practice of the present invention. Definitions of common terms in molecular biology may also be found in Rieger et al., Glossary of Genetics: Classical and Molecular, 5th edition, Springer-Verlag: New York, 1991; and Lewin, Genes V, Oxford University Press: New York, 1994.

"Single-chromosome Amplification Library";
"Member" Thereof

A "single-chromosome amplification library" is defined as a library produced by a method as described above or in the Examples below. The term "single-chromosome amplification library" is intended to embrace a library produced from either a single chromosome or a single subchromosomal fragment.

The use of the term "amplification" in "single-chromosome amplification library" is intended to include PCR and other nucleic acid amplifications methods known to those of ordinary skill in the art. The term "library" is used as a descriptive shorthand for a plurality of DNA molecules produced by amplification of a chromosome (or subchromosomal fragment, band, region, etc.) of interest, e.g., by PCR. The term "library" does not necessarily imply that such DNA molecules are cloned in a vector. For a similar use of the term "library," see, e.g., Vooijs et al., Am. J. Hum. Genet. 52:586–597, 1993. Nonetheless, a single-chromosome amplification library or members of such a library may be cloned into a vector by well-known means, if desired.

A "member" of a single-chromosome amplification library is an individual DNA molecule in such a library.

Nucleic Acids

Nucleic acids useful in the practice of the present invention comprise isolated nucleic acids from a single-chromosome amplification library according to the present invention.

The nucleic acids of the present invention may be free in solution or attached by conventional means to a solid support, such as a hybridization membrane (e.g., nitrocellulose or nylon), a bead, or other solid support known in the art. For example, libraries that are specific for a chromosome or subchromosome fragment, members of such libraries, or fragments of such library members can be used to produce chromosome "dot," "spot," or "slot" blots (see e.g., Lebo et al., Science 225:57–59, 1984).

"Isolated". An "isolated" nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic-acid purification methods. The term also embraces nucleic acids prepared by recombinant expression in a host cell as well as chemically synthesized nucleic acids.

The nucleic acids of the present invention comprise at least a minimum length able to hybridize specifically with a target nucleic acid (or a sequence complementary thereto) under stringent conditions as defined below. The length of a nucleic acid of the present invention is preferably 15 nucleotides or more, although a shorter nucleic acid may be employed as a probe or primer if it is shown to specifically hybridize under stringent conditions with a target nucleic acid by methods well known in the art.

Probes and primers. Nucleic-acid probes and primers can readily be prepared based on the nucleic acids according to the present invention. A "probe" comprises an isolated nucleic acid attached to a detectable label or reporter molecule well known in the art. Typical labels include radioactive isotopes, ligands, chemiluminescent agents, and enzymes. Methods for labeling and guidance in the choice of labels appropriate for various purposes are discussed, e.g., in *Molecular Cloning: A Laboratory Manual,* 2nd ed., vol. 1–3, ed. Sambrook et al., Cold Spring Harbor Laboratory Press: Cold Spring Harbor, N.Y., 1989; and *Current Protocols in Molecular Biology,* ed. Ausubel et al., Greene Publishing and Wiley-Interscience: New York, 1987 (with periodic updates).

"Primers" are short nucleic acids, preferably DNA oligonucleotides 15 nucleotides or more in length, which are annealed to a complementary target DNA strand by nucleic acid hybridization to form a hybrid between the primer and the target DNA strand, then extended along the target DNA strand by a polymerase, preferably a DNA polymerase. Primer pairs can be used for amplification of a nucleic acid sequence, e.g., by the polymerase chain reaction (PCR) or other nucleic-acid amplification methods well known in the art.

Methods for preparing and using probes and primers are described, for example, in Sambrook et al. (1989), Ausubel et al. (1987), and Innis et al., *PCR Protocols: A Guide to Methods and Applications,* Academic Press: San Diego (1990). PCR primer pairs can be derived from the sequence of a member of a library according to the present invention for example, by using computer programs intended for that purpose such as Primer (Version 0.5,@ 1991, Whitehead Institute for Biomedical Research, Cambridge, Mass.).

Probes or primers can be free in solution or covalently or noncovalently attached to a solid support by standard means.

Substantial similarity. A first nucleic acid is "substantially similar" to a second nucleic acid if, when optimally aligned (with appropriate nucleotide insertions or deletions) with the other nucleic acid (or its complementary strand), there is nucleotide sequence identity in at least about 75%–90% of the nucleotide bases, and preferably greater than 90% of the nucleotide bases. ("Substantial sequence complementarity" requires a similar degree of sequence complementarity.) Sequence similarity can be determined by comparing the nucleotide sequences of two nucleic acids using sequence analysis software such as the Sequence Analysis Software Package of the Genetics Computer Group, University of Wisconsin Biotechnology Center, Madison, Wis.

Operably linked. A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

"Recombinant". A "recombinant" nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Techniques for nucleic acid manipulation are described generally in, for example, Sambrook et al. (1989) and Ausubel et al. (1987, with periodic updates).

Preparation of recombinant or chemically synthesized nucleic acids; vectors, transformation, host cells. Large amounts of a nucleic acid, e.g., a member of a library of the present invention or a portion thereof, can be produced by recombinant means well known in the art or by chemical synthesis.

Natural or synthetic nucleic acids according to the present invention can be incorporated into recombinant nucleic-acid constructs, typically DNA constructs, capable of introduction into and replication in a host cell. Usually the DNA constructs will be suitable for replication in a unicellular host, such as *E. coli* or other commonly used bacteria, but may also be intended for introduction into yeast, mammalian, plant or other eukaryotic cells.

Preferably, such a nucleic-acid construct is a vector comprising a replication system recognized by the host. For the practice of the present invention, well-known compositions and techniques for preparing and using vectors, host cells, introduction of vectors into host cells, etc. are employed, as discussed in, inter alia, Sambrook et al., 1989, or Ausubel et al., 1987. A cell into which has been introduced a foreign nucleic acid, such as a recombinant vector, is considered "transformed." Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers.

Nucleic Acid Hybridization; "Stringent Conditions"; "Specific"

The nucleic acid probes and primers of the present invention hybridize under stringent conditions to a target DNA sequence, e.g., to a particular chromosome or subchromosomal region, band, etc.

The term "stringent conditions" is functionally defined with regard to the hybridization of a nucleic-acid probe to a target nucleic acid (i.e., to a particular nucleic-acid sequence of interest) by the hybridization procedure discussed in Sambrook et al., 1989 at 9.52–9.55. See also, Sambrook et al., 1989 at 9.47–9.52, 9.56–9.58; Kanehisa, Nuc. Acids Res. 12:203–213, 1984; and Wetmur and Davidson, J. Mol. Biol. 31:349–370, 1968.

Regarding the amplification of a target nucleic-acid sequence (e.g., by PCR) using a particular amplification primer pair, stringent conditions are conditions that permit the primer pair to hybridize only to the target nucleic-acid sequence to which a primer having the corresponding wild-type sequence (or its complement) would bind.

Nucleic-acid hybridization is affected by such conditions as salt concentration, temperature, or organic solvents, in addition to the base composition, length of the complementary strands, and the number of nucleotide-base mismatches between the hybridizing nucleic acids, as will be readily appreciated by those skilled in the art.

When referring to a probe or primer, the term "specific for (a target sequence)" indicates that the probe or primer hybridizes under stringent conditions only to the target sequence in a given sample comprising the target sequence.

Nucleic Acid Amplification

As used herein, "amplified DNA" refers to the product of nucleic acid amplification of a target nucleic-acid sequence. Nucleic-acid amplification can be accomplished by any of the various nucleic-acid amplification methods known in the art, including the polymerase chain reaction (PCR). A variety of PCR methods are described in, inter alia, U.S. Pat. Nos. 4,683,195 and 4,683,202 and in PCR Protocols: A Guide to Methods and Applications, Innis et al. eds., Academic Press, San Diego, 1990. A preferred amplification method is the ligation-adaptor PCR technique (Chang et al., Genomics 12:307–312, 1992; Lisitsyn et al., Science 259:946–951, 1993; Jinno et al., J. Biochem. Jul. 112:75–80, 1992).

In Situ Hybridization; Evaluation of Chromosomal Abnormalities

A number of techniques have been developed in which nucleic acid probes are used to locate specific DNA sequences on intact chromosomes in situ, a procedure called "in situ hybridization." See, e.g., Pinkel et al., Proc. Natl. Acad. Sci. USA 85:9138–9142, 1988 (regarding FISH), and Lengauer et al., Hum. Mol. Genet. 2:505–512, 1993 (regarding "chromosomal bar codes"). Well-known methods for in situ hybridization and for the preparation of probes or primers for such methods are employed in the practice of the present invention, including direct and indirect in situ hybridization methods.

FISH has played an important role as a cytogenetic tool in identifying chromosomes, detecting chromosomal abnormalities, and determining the number, size, and location of specific DNA sequences in mammalian cells (Pinkel et al., Proc. Natl. Acad. Sci. USA 85:9138–9142, 1988). In FISH, a probe is chemically labeled with a fluorescent reporter molecule, then hybridized to a chromosomal target sequence in a metaphase chromosome or interphase nuclei. The location of the probe, and thus of the target sequence, is determined using fluorescence microscopy.

Multicolor probe labeling permits simultaneous use of several different probes inside a cell, allowing the researcher to simultaneously analyze multiple target sequences. Fluorescence microscopes employing high-transmission objectives and multiple filters are available for such purposes.

The invention will be better understood by reference to the following Examples, which are intended to merely illustrate the best mode now known for practicing the invention. The scope of the invention is not to be considered limited thereto, however.

EXAMPLES

Example 1

Preparation and Screening Single-chromosome Amplification Libraries from Human Chromosomes 8–12 and X Cells and cell lines. Human peripheral blood lymphocytes (PBL) were grown in RPMI 1640 medium (GIBCO/BRL, Grand Island, N.Y.), supplemented with 16% fetal bovine serum (GIBCO/BRL, Grand Island, N.Y.).

Single-chromosome sorting. Chromosomes were prepared by a standard polyamine buffer method (Young et al., Proc. Natl. Acad. Sci., USA 77:7727–7731, 1981) and labeled with 10 µg/ml DAPI (Accurate Chemical and Scientific, Westbury, N.Y.). Sorting was performed on an Ortho 50 HH cytofluorograph (Ortho Diagnostic Systems, Westwood, Mass.) using 100 mW of 351–364 nm excitation. Single chromosomes within the desired fluorescence intensity range were sorted such that each chromosome was delivered into a siliconized 0.5-ml PCR tube containing 3 µl water overlaid with mineral oil. The tubes were subsequently centrifuged at 5,000 rpm for 10 min. and stored at −20° C.

DNA extraction, digestion, adaptor ligation, and PCR amplification. Mineral oil above the sorted samples was removed and sample volumes were adjusted to 10 Al with 50 ng/µl Proteinase K (Boehringer Mannheim Biochemicals, Indianapolis, Ind.), 10 mM Tris, pH 7.5. After incubation at 50° C. for one hr, the enzyme was inactivated with 40 ng/µl phenylmethylsulfonyl fluoride (PMSF, Sigma Chemical, St. Louis, Mo.) at 50° C. for one hr. PMSF was then inactivated by heating at 65° C. for three hr. Sau3AI restriction endonuclease (Promega, Madison, Wis.) was added at 0.02 unit/µl after adjusting the buffer to 100 mM Tris, pH 7.2 by addition of 1.5 µl of lox buffer B (Promega, Madison, Wis.), 10 mM $MgCl_2$ and 100 ng/µl bovine serum albumin in a total volume of 15 µl. After overnight incubation at 37° C., the enzyme was inactivated by heating at 65° C. for 20 min.

Ligation-adaptor PCR amplification was performed using adaptor oligonucleotides R Bgl 24 and R Bgl 12 as described previously (Lisitsyn et al., Science 259:946–951, 1993) with some modification for the microamplification. Briefly, 0.5 µM adaptor in 10 mM Tris HCl, 10 mM $MgCl_2$, 5 mM 2-mercaptoethanol, 2 mM ATP was added and incubated with 3 Weiss Unit/µl of T4 DNA ligase (30 Weiss Unit/µl, New England Biolabs, Beverly, Mass.) in a 20 µl total volume. The ligation mix was incubated at 16° C. overnight, then PCR-amplified by adding the ligation mix to 99 µl of a solution containing 200 µM of each dNTP, 1 µM R Bgl 24, 50 mM KCl, 10 mM Tris-HCl (pH 8.2), 1.5 MM $MgCl_2$ and 3 U of Taq polymerase (Promega, Madison, Wis.). The mixtures were incubated for 5 min. at 72° C. in a thermocycler (Perkin-Elmer Cetus, Norwalk, Conn.) to fill in 3' ends, followed by 42 cycles of 1 min. at 95° C., and 4 min. at 72° C. and one cycle of 10 min. at 72° C. PCR products (10 µl/sample) were analyzed on 2% agarose gels stained with ethidium bromide. Some libraries were further amplified to a total of 84 cycles, to determine the effect of extended PCR amplification.

Chromosome painting by fluorescence in situ hybridization (FISH). PCR products (100 ng each) were biotinylated by nick translation and hybridized in situ to denatured metaphase chromosome spreads for 48 hours (VanDevanter and Yirdaw, Genes, Chromosomes and Cancer 6:190–197, 1993). Human repetitive elements were suppressed with 50 µg human Cot-1 DNA (GIBCO/BRL, Grand Island, N.Y.) per 10 µl hybridization. Slides were washed (Yunis and Prakash, Science 215:1525–1530, 1982) and blocked for 10 minutes with 4X SSC, 1% BSA (Sigma), 5% nonfat dry milk at room temperature. Probes were localized by 30 minutes incubation with 25 µg/ml Texas Red-labeled avidin (Vector Laboratories, Burlingame, Calif.) in 100 µl 4X SSC, 1% BSA at room temperature. Unbound Texas Red-labeled avidin was removed by washing slides sequentially with 4X SSC, 4X SSC/0.1% Triton X-100, and 4X SSC for 3 min. each. Chromosomes were counterstained by draining slides thoroughly and coverslipping with antifade solution (Vector Laboratories, Burlingame, Calif.) containing 15 µg/ml DAPI. Alternatively, fluorescent chromosome R-bands were generated with chromomycin A3/distamycin A (Magenis et al., Genomics 11:346–351, 1991).

Chromophores were visualized by epifluorescence using a 100X Zeiss neofluor objective on a Nikon Optiphot microscope with independent excitation, and images were digitally recorded (VanDevanter et al., Genes, Chromosomes and Cancer 6:190–197, 1993).

DNA fragment sizes in these libraries appeared as a continuum from 200 to about 1000 bp after 42 cycles of PCR amplification, with a total DNA yield of 1–2 µg.

Human chromosome libraries from chromosomes 8–12 and X were generated by sorting and PCR amplifying a single chromosome. No attempt was made to resolve overlapping chromosomes in the region of smaller C group chromosomes. Chromosome libraries for human chromosomes 8–11 and X were identified by FISH. This strategy resulted in pure chromosome-specific libraries even when the chromosome population could not be separately resolved by flow cytometry.

Extended PCR amplification (an additional 42 cycles) appeared to decrease the relative homogeneity of FISH signals across chromosomes. In some cases the average size and complexity of the libraries were reduced. The magnitude of this effect varied from sample to sample, although in most cases the homogeneity of chromosome labeling was only marginally reduced.

Occasionally, FISH patterns showed regions of under-representation, which may have resulted either from unusual distributions of Sau3AI restriction sites or unequal restriction digestion. In some cases, pseudo-banding patterns have been generated after 84 or 126 cycles of PCR. These pseudo-banding patterns can be used to supplement R-banded counterstaining to assist in region identification and in the orientation of translocated and inverted chromosome regions. In extreme cases region- or "band"-specific probes can be made.

Smaller sized fragments are kinetically enriched during PCR since the polymerase replicates shorter sequences more rapidly and reliably. It is possible that decreased sequence representation in some extensively amplified libraries is a result of the loss of larger single-copy sequences. Repetitive sequences may also be relatively more abundant in the smaller fragments.

Smaller sized fragments can be selected against, e.g., by any of the various size-selection methods known in the art. For example, this can be accomplished by agarose gel electrophoresis of PCR products after 42 cycles, isolating larger fragments from the gel, purifying the fragments, e.g., by using sodium iodine/glass milk (GeneClean II, Intermountain Scientific Corp., Bountiful, Utah), and amplifying the larger fragments by PCR for an additional 42 cycles.

FISH analyses of these libraries demonstrated that over half of all products exhibited apparently pure painting of entire individual chromosomes. FISH on normal human metaphase spreads using fluorescein-labeled PCR products after biotinylation demonstrated the high quality and specificity of labeling from a sorted chromosome. Even though no attempt was made to resolve any of the overlapping chromosome fluorescence peaks in the flow-histogram, approximately 65% of individually sorted chromosomes yielded satisfactory FISH results.

Replication of repetitive sequences probably competes with amplification of unique sequences during extensive PCR. Since the repetitive sequences are not desired (their hybridization is blocked during FISH, for example), depleting this fraction of the library early in PCR amplification likely maximizes representation of single-copy sequences. In addition, the absence of repetitive DNA is advantageous in reducing the requirement for blocking DNA in FISH and in reducing the proportion of repetitive products if the PCR DNA libraries are cloned.

Among the methods that can be used for depleting the libraries of repetitive sequences are the following:

a) Restriction of Cot-1 DNA. After 10 PCR cycles of initial chromosome amplification, Taq is removed by phenol extraction of DNA, the DNA is denatured, and then renatured under Cot-1 conditions (only repetitive sequences anneal). The restriction enzyme Sau3A is added to remove the ligation-adaptor primer sequences by restriction at the ligation site. Repetitive sequences thus no longer contain PCR priming sequences. Nucleotides, primers, and Taq are added again and PCR is continued, selectively amplifying non-repetitive sequences.

b) Subtraction by Representational Difference Analysis (RDA). The RDA protocol is essentially as described (Lisitsyn et al., Science 259:946–951, 1993). Cot-1 DNA (Boehringer Mannheim Biochemicals, Indianapolis, Ind.) is used as Driver and twenty-cycle single-chromosome PCR is used as Tester DNA. Both are digested with Sau3AI (the Driver to select these fragments, the Tester to remove adaptors previously ligated on). Both Driver and Tester amplicons are phenol and phenol/chloroform extracted, ethanol precipitated, and resuspended in Tris-EDTA buffer.

A portion of the Tester amplicon digest is purified away from the adaptors by running 10 µg of the digest on an agarose gel, cutting out fragments between 150–1500 bp, and eluting the product using a Qiagen DNA purification kit (Qiagen Inc., Chatsworth, Calif.). A second set of 24 bp oligonucleotide adaptors is ligated to 2 µg of the gel purified Tester amplicon. 40 µg of Driver amplicon and 0.4 µg of Tester amplicon ligate are combined, phenol/chloroform extracted, and ethanol precipitated, then resuspended in 4 µl 3x EE buffer (Strauss and Ausubel, Proc. Natl. Acad. Sci. USA 87:1889–1893, 1990). This suspension is overlaid with mineral oil and denatured at 98° C. for three minutes. 5M NaCl is added and the sample is allowed to hybridize at 67° C. for forty hours.

The Driver/Tester hybridization mixture is diluted with 390 µl of TE buffer, 40 µl of which is incubated with Taq polymerase in 400 µl PCR buffer containing dNTPs to fill in the ends of the rehybridized tester. This is used as the template for ten cycles of selective amplification using the same second set of 24-bp oligonucleotides as primers. The amplificate is then phenol- and phenol/chloroform-extracted, ethanol precipitated, and resuspended in 20 μl water and 20 μl 2x Mung Bean nuclease buffer. Mung Bean nuclease-treated product is diluted in 160 μl TE pH 8.9 and the enzyme inactivated by a five-minute incubation at 98° C. 40 μl of this mixture is amplified for twenty-five further cycles of PCR, thus producing a "first round" difference product. At this stage, the product may be evaluated for use in FISH and molecular studies.

If needed, a second-round difference product can be made by digesting with Sau3AI, extracting with phenol and phenol/chloroform, precipitating with ethanol, and ligating a third set of oligonucleotide adaptors to the digested first-round difference product. The next hybridization/amplification step uses 40 μg of Driver amplicon DNA digest and 50 ng of adaptor-ligated difference product and follows the above method of concentration, hybridization, and selective amplification. Driver:Driver hybrids lack PCR primers; Driver:Tester hybrids have only one end containing primer and thus do not serve as a substrate for subsequent exponential PCR. Only Tester:Tester hybrids, which do not contain repetitive sequences, have primer on both ends and are amplified.

Example 2

Identification of Human Chromosomes Carrying STRP Markers

A sorting experiment was performed on human SR lymphocytes (Beighle et al., Hum. Genet. 38:113–121, 1977), which carry differently sized short tandem repeat polymorphism (STRP) markers (D8S201; Tomfohrde et al., Genomics 14:144–152, 1992) on the short arm of chromosome 8. The procedure followed was essentially as described above.

The human lymphoblastoid line SR (Beighle et al., Hum. Genet. 38:113–121, 1977) was grown in RPMI 1640 medium (GIBCO/BRL, Grand Island, N.Y.), supplemented with 16% fetal bovine serum (GIBCO/BRL, Grand Island, N.Y.). PCR products (50 ng DNA in 2.5-μl volumes) obtained by sorting and amplifying individual C group chromosomes of the human lymphoblastoid line SR were diluted to 50 μl containing 25 MM $MgCl_2$, 200 μM of each dNTP, 1 unit of Tag DNA polymerase and 100 ng of each D8S201 primer (Tomfohrde et al., Genomics 14:144–152, 1992). The reaction mixture was overlaid with mineral oil and amplified by "touch down" PCR (Don et al., Nucleic Acids Res. 19:4008, 1991) with cycles of 20 sec at 98° C., 1 min. at the annealing temperature, then 40 seconds at 72° C. with the annealing temperature decreased from 72° C. to 61° C. by 1° C. every other cycle. Four cycles with the annealing temperature at 60° C., then 9 cycles with annealing at 58° C. were then performed. 0.5 μl of alpha[$^{32}$P]-dCTP at 3000 Ci/mMol (Amersham Corp., Arlington Heights, Ill.) was added and two more cycles with 60° C. annealing temperature were performed. PCR products were fractionated on a 6% denaturing polyacrylamide gel at 1700 volts for approximately 3 hr. Total genomic DNA from the SR line was run as a positive control.

Of 22 libraries screened for D8S201 alleles prior to FISH analyses, three (E101, E105, and E111) showed either the small or large D8S201 allele, and no sample showed both alleles. Subsequent FISH analyses confirmed that E101, E105, and E111 were specific for chromosome 8.

These results demonstrate that a desired chromosome can be identified by molecular screening of large numbers of single-chromosome amplification libraries and that the STRPs used in mapping studies are represented in these libraries. This type of screening also assists the rapid assembly of complete chromosome libraries.

Example 3

Region-Specific Sub-Chromosomal Libraries from Human Chromosomes 1 and 2

Region-specific human libraries were obtained by sorting approximately 10,000 human #1 and #2 chromosomes as described above, then shearing DNA isolated from single chromosomes using a 30-gauge needle to generate fragments of each chromosome. Individual fragments each having a DNA content representing approximately 10% of the intact chromosomes were individually sorted, and single fragments were PCR-amplified as described above.

FISH analyses of the libraries showed localization to distal regions of these chromosomes in a majority of samples. For example, a library produced from a single flow-sorted fragment of human chromosome 1 was localized to a distal region of 1p.

Mechanical breakage is useful for preparing subchromosomal libraries of such distal regions. To obtain fragments that are less enriched in regions of chromosomes subject to mechanical breakage, chromosomes can be treated with agents known to cause DNA-strand breakage and fragmentation, e.g., gamma irradiation (von Sonntag, Basic Life Sci. 57:287–317, 1991) and bleomycin (Hsu and Cherry, Cancer Genet. and Cytogenet. 17:307–313, 1985), digested with restriction enzymes having infrequent (e.g., 8-base) recognition sites, or by other well-known methods.

The size of the sub-chromosomal fragments can be precisely preselected by choosing the DNA fluorescence intensity used for flow sorting. The sorting window can be changed to sort for smaller fragment sizes, in which case the detectability of sub-band specific markers by FISH can be maximized by employing different means for fluorochrome labeling (e.g., PCR incorporation vs. nick-translation or the use of signal amplification by avidin-biotin complex).

Example 4

Single-chromosome Amplification Libraries Generated from Non-Human (Baboon and Canine) Chromosomes Baboon (P. cynocephalus), and canine peripheral blood limphocytes (PBL) were obtained by venipuncture. PBL cultures were stimulated with phytohemagglutinin (baboon) (DIFCO Laboratories, Detroit, Mich.) or concanavalin A (canine) (DIFCO Laboratories, Detroit, Mich.) for 72 hr to produce metaphase cells. Baboon and canine repeats were suppressed with 50 μg of baboon or canine genomic DNA, respectively.

Sorting and PCR amplification of a single baboon chromosome yielded single-chromosome amplification libraries, such as B707, which hybridized to baboon chromosome 19. Similarly, the canine chromosome library D305 hybridized to a unique pair of somatic canine chromosomes. The utility of these non-human libraries for comparative cytogenetic studies is demonstrated by the results of cross-hybridization of the baboon B707 library to human chromosomes: B707 consistently hybridized to all but the distal P arm of the human 19, showing the apparent homology of these two primate chromosomes. Similar cross-hybridization patterns have been observed with other baboon chromosome libraries. Five of eight PCR-amplified baboon chromosomes yielded high-quality chromosome-specific probes. Hybridization of other baboon probes to human metaphase chromosomes identified homologous chromosome regions with various evolutionary translocations and inversions.

The specificity of the single-chromosome amplification library for a single chromosome is assured even when different chromosomes cannot be separated into pure populations by flow cytometry, because each library is generated from a single sorted chromosome (or fragment). This property was essential for the generation of baboon and canine single-chromosome amplification libraries, since the flow histograms for these species precluded purification of unique chromosome pools by sorting, unless somatic-cell hybrids were used. No special expertise or instrumentation for chromosome sorting was required, since representative sequences could be obtained from technically poor chromosome resolution by cytometry.

Example 5

Cytogenetic Analysis of an Abnormal Marker Chromosome in a Transformed Human Keratinocyte Cell Line The human papilloma virus type 18-transformed foreskin keratinocyte cell line FEP-1811 (Smith et al., Int. J. Cancer, 44:1124–1131, 1989) was grown in keratinocyte serum-free medium (GIBCO/BRL, Grand Island, N.Y.).

Conventional cytogenetic examination of the HPV-18-transformed keratinocyte cell line FEP-1811 indicated the presence of a marker chromosome larger than chromosome 1 with a banding pattern consistent with most of chromosome 3 (Smith et al., Int. J. Cancer 44:1124–1131, 1989). Additional material within the marker could not be identified by conventional banding. In order to generate marker-chromosome specific DNA libraries for characterization of unidentified regions within the marker, individual events corresponding to the estimated DNA content of this marker (slightly larger than chromosome 1) were flow-sorted, PCR amplified, and hybridized to normal human metaphase chromosomes.

One quarter of the PCR products analyzed by FISH showed hybridization patterns identical to those of library K133, in which all of chromosome 3 and distal regions of chromosomes 13 and 21 were painted.

The remaining PCR products painted a diverse spectrum of multiple smaller chromosomes, with each library painting a different set of chromosomes. This result suggests that 3/4 of the libraries generated were simple aggregates of normal chromosomes, and that ¼ of the libraries were of the specific marker chromosome. Subsequent FISH of library K133 back to FEP-1811 metaphase chromosomes demonstrated labeling of the entire marker in question, as well as segments of chromosome 13 and 21.

Example 6

Use of Chromosome-Specific Alphoid Sequences to Screen for Libraries Specific for a Desired Chromosome To increase the yield of libraries from one desired chromosome without relying on screening by FISH, chromosome-specific alphoid (chromosome-specific repeat) sequences were used as a probe for Southern hybridization to chromosome PCR products. The presence of hybridization label in the lanes containing DNA from single chromosome 8 amplification libraries indicates the chromosome-8 origin of the libraries. Large numbers of single-chromosome amplification libraries can be simultaneously screened in this manner.

Example 7

Selective Identification of Microsatellite Repeat Sequences Present in Non-human Chromosome Libraries Canine libraries D305 and D304, sorted and amplified as described above, were used to make chromosome-specific $(CA)_n$ repeat libraries. Approximately 40 ng of canine DNA was digested with Sau3A. Oligonucleotides were removed by precipitation with ammonium acetate, followed by two precipitations with sodium acetate. Samples were resuspended and cloned in the BamHI site of BlueScript (Stratagene Cloning Systems, La Jolla, Calif.), which had been treated with calf-intestinal phosphatase (Stratagene Cloning Systems, La Jolla, Calif.). One-tenth of the library was plated, lifted onto filters and screened using a $(CA)_{15}$ oligonucleotide (regarding $(CA)_n$ repeats, see Stallings et al., Genomics 10:807–815, 1991 and Beckman and Weber, Genomics 12:627–631, 1992) which had been end-labeled using $\gamma^{32}P$-dATP and T4 polynucleotide kinase (Stratagene Cloning Systems, La Jolla, Calif.). Approximately 30 (CA) repeat-containing clones resulted from this screen.

Nucleotide-sequence information derived from these clones is used to define primer sequences which bracket each $(CA)_n$ repeat. Since average-sized chromosomes (e.g., in dog and mouse) are about 60–100 megabases in length, the ability to define even 100 markers per chromosome permits the construction of high-density maps of each chromosome.

This protocol may be modified in order to improve its efficiency. The amplified material ranges in size from 200 to about 1000 bp. The most efficient substrate for making small-insert libraries for the purpose of constructing genetic maps range in size from 300–800 bp. Smaller pieces are generally too short to ensure that PCR primers can be made which define the repeat unit. Thus, the 300–800 bp fragments are cut out of the agar gel and purified using sodium iodine/glass milk (GeneClean II) according to manufacturer's instructions.

Example 8

Chromosome "Spot Blots"

Chromosome-specific microsatellite repeat or alphoid-repeat sequences are useful markers for screening and identifying the chromosomal origin of libraries derived from single sorted chromosomes. However, the gels used to evaluate these results are somewhat slow and labor-intensive. A more rapid procedure for screening (or prescreening) the origin of DNA libraries produced from single sorted chromosomes is the use of dot-blot arrays of chromosome-specific DNA.

In order to identify which products were specific for chromosome 8, thirty different single-chromosome amplification libraries were dotted onto a nylon membrane (100 ng DNA per spot) and UV cross-linked. The membrane was hybridized to a $^{32}P$-labeled PCR product from human chromosome 8. PCR primers used for amplification of this chromosome-8 library were different than those used for PCR of the unknown chromosomes in order to eliminate potential hybridization complementarity. The primers used were RBgl and NBgl (Lisitsyn et al., Science 259:946–951, 1993).

Several dots (libraries 21 and 29) were strongly positive, a few (e.g., library 28) were weakly positive, and most were negative. Libraries 28 and 23 were confirmed by FISH to indeed arise from the amplification of chromosome 8. Library 21 was produced by PCR amplification of DNA from ten sorted chromosomes that were pooled then amplified. At least one chromosome 8 was included to serve as the positive "control." Chromosome 8 comprised 25–30% of all chromosomes in this sorted region. Therefore, it was assumed that ten sorted chromosomes would include at least one chromosome 8. Libraries 25–27 are not chromosome 8-specific libraries.

There was a slight amount of non-specific hybridization to library 26 (a chromosome-12 library) which was not seen on a repeat blot. This weak hybridization may have occurred due to cross-hybridization with a repeated sequence that was insufficiently blocked by the presence of Cot1 DNA. Some Sau3A-restricted and amplified repetitive sequences may be much more extensively represented in the libraries than in genomic Cot1 DNA, making it more difficult to block these sequences. This problem can be overcome, for example, by using Sau3A-restricted and ligation PCR-amplified Cot1 DNA.

All publications and published patent documents cited in this specification are incorporated herein by reference to the same extent as if each individual publication or patent application was specifically and individually indicated to be incorporated by reference.

This invention has been detailed both by example and by direct description. It should be apparent that one having ordinary skill in the relevant art would be able to surmise equivalents to the invention as described in the claims which follow but which would be within the spirit of the foregoing description. Those equivalents are to be included within the scope of this invention.

What is claimed is:

1. A method of producing a single-chromosome amplification library corresponding to a target chromosome or subchromosomal fragment, the method comprising the steps of:
   (a) providing a population of chromosomes or subchromosomal fragments from a chromosome source comprising a target chromosome or subchromosomal fragment;
   (b) flow sorting the population, thereby providing a single isolated chromosome or subchromosomal fragment at each of a plurality of locations;
   (c) producing a set of fragments of each of the single isolated chromosomes or subchromosomal fragments;
   (d) performing an amplification reaction on each set of fragments, thereby producing a plurality of libraries, each library comprising an amplification product corresponding to a respective set of fragments; and
   (e) screening the plurality of libraries to identify a library that is specific for the target chromosome or subchromosomal fragment.

2. The method of claim 1 wherein the amplification reaction employs an amplification primer specific for the target chromosome or subchromosomal fragment.

3. The method of claim 1 wherein step (e) comprises hybridizing the plurality of libraries with a probe specific for the target chromosome or subchromosomal fragment.

4. The method of claim 1 wherein each of the DNA fragments produced in step (c) has two ends and the method further comprises the step of adding an adaptor to each of the ends of each DNA fragment.

5. The method of claim 1 wherein the target chromosome or subchromosomal fragment is mammalian.

6. The method of claim 5 wherein the target chromosome or subchromosomal fragment is human.

7. The method of claim 1 wherein the chromosome source is a primary tumor culture or a solid tumor.

8. A method of producing a library that is specific for a desired region of a target chromosome, the method comprising the steps of:
   (a) providing a population of fragments of the target chromosome;
   (b) flow sorting the population, thereby providing a single isolated fragment of the target chromosome at each of a plurality of locations;
   (c) producing a set of subfragments of each single isolated fragment;
   (d) performing an amplification reaction on each set of subfragments, thereby producing a plurality of libraries, each library comprising an amplification product corresponding to a respective set of subfragments;
   (e) hybridizing the plurality of libraries with the target chromosome under stringent conditions; and
   (f) identifying a library that is specific for the desired region of the target chromosome.

9. The method of claim 8 wherein the step of hybridizing comprises in situ hybridization.

10. The method of claim 8 wherein the location is a chromosome band.

11. The method of claim 1 wherein step (e) further comprises labeling each of the plurality of libraries to produce a plurality of labeled libraries and hybridizing each of the labeled libraries to DNA of the target chromosome.

12. The method of claim 11 wherein step (e) further comprises in situ hybridization of the labeled libraries to the target chromosome.

13. The method of claim 11 wherein step (e) further comprises hybridizing the labeled libraries to a chromosome spot blot.

14. A method according to claim 1 wherein the specific library identified in step (e) has an average insert size of at least 200 base pairs.

15. A method according to claim 8 wherein the specific library identified in step (f) has an average insert size of at least 200 base pairs.

* * * * *

UNITED STATES PATENT AND TRADEMARK OFFICE
CERTIFICATE OF CORRECTION

PATENT NO. : 5,814,444

DATED : September 29, 1998

INVENTOR(S) :
PETER S. RABINOVITCH

It is certified that error appears in the above-indentified patent and that said Letters Patent is hereby corrected as shown below:

On the Cover Page:

Item [54], in the title of the application, "AMPLFICATION" should be --AMPLIFICATION--.

Column 1, line 1, in the title of the application, "AMPLFICATION" should be --AMPLIFICATION--.

Column 11, line 60, "@" should be --©--.

Column 14, line 32, "10 Al" should be --10 µl--.

Column 14, line 41, "1ox" should be --10x--.

Column 15, line 22, "10OX" should be --100X--.

Column 17, line 42, "25 MM" should be --25 mM--.

Signed and Sealed this

Fifth Day of October, 1999

Attest:

Q. TODD DICKINSON

Attesting Officer

Acting Commissioner of Patents and Trademarks